US010928308B2

(12) United States Patent
Cerignoli et al.

(10) Patent No.: US 10,928,308 B2
(45) Date of Patent: *Feb. 23, 2021

(54) ANALYSIS OF ACTION POTENTIALS, TRANSIENTS, AND ION FLUX IN EXCITABLE CELLS

(71) Applicant: Vala Sciences, Inc., San Diego, CA (US)

(72) Inventors: Fabio Cerignoli, San Diego, CA (US); Piyush Gehalot, San Diego, CA (US); Patrick M. McDonough, San Diego, CA (US); Jeffrey H. Price, San Diego, CA (US); Ross J. Whittaker, San Diego, CA (US)

(73) Assignee: Vala Sciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/511,050

(22) Filed: Jul. 15, 2019

(65) Prior Publication Data

US 2019/0353586 A1    Nov. 21, 2019

Related U.S. Application Data

(63) Continuation of application No. 15/947,490, filed on Apr. 6, 2018, now Pat. No. 10,359,357, which is a (Continued)

(51) Int. Cl.
*G01N 21/27* (2006.01)
*G02B 21/36* (2006.01)
(Continued)

(52) U.S. Cl.
CPC .......... *G01N 21/272* (2013.01); *G01J 3/2823* (2013.01); *G01J 3/4406* (2013.01);
(Continued)

(58) Field of Classification Search
CPC .... G01N 21/272; H04N 5/91; H04N 5/23212; G02B 21/365
(Continued)

(56) References Cited

U.S. PATENT DOCUMENTS

| 5,149,972 A | 9/1992 | Fay et al. |
| 6,400,487 B1 | 6/2002 | Harris et al. |

(Continued)

FOREIGN PATENT DOCUMENTS

| EP | 2932238 B2 | 2/2018 |
| WO | WO-2014-093980 | 6/2014 |

OTHER PUBLICATIONS

International Preliminary Report on Patentability in PCT/US2013/075488, dated Jun. 16, 2015, 12 pgs.
(Continued)

*Primary Examiner* — Nam D Pham
(74) *Attorney, Agent, or Firm* — Terrance A. Meador

(57) ABSTRACT

Video recordings from two or more optical channels are produced, processed, and analyzed simultaneously in order to provide quantitative analysis of action potentials, calcium transients and ionic flux in excitable cells loaded with voltage or ion sensitive dyes with distinct excitation and emission wavelengths. The specific wavelengths of fluorescent light emitted from each dye are separated and recorded. The recordings are mutually registered and cytometric analysis is performed to provide a quantitative analysis of the action potentials, calcium transient, and/or ionic flux on a cell-by-cell and well-by-well basis in microtiter plates. The cells are then fixed, labeled for other biomarkers, and scanned again. The resulting fixed cell images are registered with the live cell recordings and analyzed; missing cells that (Continued)

were washed off are detected relative to the live recordings, and cytometry data from live and fixed cell scans is collated cell-by-cell.

9 Claims, 15 Drawing Sheets

Related U.S. Application Data continuation of application No. 14/651,644, filed as application No. PCT/US2013/075488 on Dec. 16, 2013, now Pat. No. 9,939,372.

(60) Provisional application No. 61/737,663, filed on Dec. 14, 2012.

(51) Int. Cl.
| | |
|---|---|
| *H04N 5/247* | (2006.01) |
| *H04N 5/232* | (2006.01) |
| *H04N 5/91* | (2006.01) |
| *G01J 3/28* | (2006.01) |
| *G01J 3/44* | (2006.01) |
| *G01N 21/64* | (2006.01) |
| *G01N 33/52* | (2006.01) |

(52) U.S. Cl.
CPC ..... *G01N 21/6408* (2013.01); *G01N 21/6428* (2013.01); *G01N 21/6458* (2013.01); *G01N 33/52* (2013.01); *G02B 21/365* (2013.01); *H04N 5/23212* (2013.01); *H04N 5/232133* (2018.08); *H04N 5/247* (2013.01); *H04N 5/91* (2013.01); *G01N 2021/6421* (2013.01); *G01N 2021/6441* (2013.01)

(58) Field of Classification Search
USPC .......................................... 348/79
See application file for complete search history.

(56) References Cited

U.S. PATENT DOCUMENTS

| | | | |
|---|---|---|---|
| 6,682,927 | B2 | 1/2004 | Meyer et al. |
| 6,839,469 | B2 | 1/2005 | Nguyen et al. |
| 7,469,056 | B2 | 12/2008 | Ramm et al. |
| 7,615,356 | B2 | 11/2009 | Maher et al. |
| 7,655,434 | B2 | 2/2010 | Jones et al. |
| 7,957,911 | B2 | 6/2011 | Harris et al. |
| 7,978,885 | B2 | 7/2011 | Arini et al. |
| 8,179,597 | B2 | 5/2012 | Namba et al. |
| 8,318,488 | B1 | 11/2012 | Bohlen et al. |
| 8,385,624 | B2 | 2/2013 | Charlot et al. |
| 9,939,372 | B2 | 4/2018 | Cerignoli et al. |
| 10,359,357 | B2 | 7/2019 | Cerignoli et al. |
| 2005/0051723 | A1 | 3/2005 | Neagle et al. |
| 2005/0233356 | A1 | 10/2005 | Jones et al. |
| 2006/0147901 | A1 | 7/2006 | Jan et al. |
| 2007/0016373 | A1 | 1/2007 | Hunter et al. |
| 2008/0044879 | A1 | 2/2008 | Harjes et al. |
| 2008/0144895 | A1 | 6/2008 | Hunter et al. |
| 2010/0289887 | A1 | 11/2010 | Charlot et al. |
| 2011/0226962 | A1 | 9/2011 | Knebel |
| 2011/0318775 | A1 | 12/2011 | Mercola et al. |
| 2012/0092546 | A1 | 4/2012 | Borovytsky |
| 2013/0244318 | A1 | 9/2013 | Chariot et al. |
| 2015/0330892 | A1 | 11/2015 | Cerignoli et al. |

OTHER PUBLICATIONS

European Search Report in EPA 13862952.2-1554, dated Nov. 15, 2015, 9 pgs.

Response to European Search Report in EPA 138629521-1554, dated Jun. 8, 2016, 14 pgs.

Teruel, M.N. and Meyer, T., Parallel single-cell monitoring of receptor-triggered membrane translocation of a calcium-sensing protein module. *Science*, 2002;295:1910-1912.

Bers, D.M. Cardiac excitation-contraction coupling. *Nature*. 2002,415:198-205.

Mummery, C., Ward-van Oostwarrd, D., et al, Differentiation of Human Embryonic Stem Cells to Cardiomyocytes: Role of Coculture with Visceral Endoderm-Like Cells. *Circulation*. 2003;107:2733-2740.

Mery, A., Almond, F., et al. Initiation of Embryonic Cardiac Pacemaker Activity by Inositol 1,4,5-Triphosphate-dependent Calcium Signaling. *Mol. Bio. of the Cell*, 2005;16:2414-2423.

Grey, C., Mery, A., et al. Fine-tuning homeostasis underlies progression of cardiomyopathy in myocytes derived from genetically modified embryonic stem cells. *Hum. Mol. Gen*. 2005;14,10:1367-1377.

Dolnikov, K., Shilkrut, M., et al. Functional properties of human embryonic stem cell-derived cardiomyocytes. *Ann. N.Y. Acad. Sci*. 2005;1047:66-75.

Fast, V. Simultaneous optical imaging of membrane potential and intracellular calcium. *J. of Elect*.2005; 38:107-112.

Kaspar E. Vogt, et al., "High-resolution simultaneous voltage and Ca 2+ imaging", *J. Physiol*, 589 3 (2011) pp. 489-494.

Saurabh R. Sinha, et al., "Simultaneous optical recording of evoked and spontaneous transients of membrane potential and intracellular calcium concentration with high spatio-temporal resolution", *J. Neuroscience Methods* 80 (1995) pp. 49-60.

Simultaneous imaging of the same FOV for two distinct fluorescent signals

Live cell images: Nuclei (left) and calcium (right)

Fixed cell images: Nuclei (left) and α-actinin (right). Note shift – see arc in each.

*Live cells images: Nuclei (left) and calcium (right)*

*Fixed cell images: Nuclei (left) and α-actinin (right)*

*Nuclear segmentation of live cell image (left) and fixed cell image (right)*

*Live cell images: Nuclei (left) and calcium (right) - post-fixed missing nuclei removed*

*Fixed cell images: Nuclei (left) and α-actinin (right)*

*Nuclear segmentation of live cell image missing nuclei removed (left) and fixed cell image (right)*

| Cell ID | API PI WM | Ci on Cm API Decay Time | Ci on Cm API FWHM Time | Ci on Cm API Peak Value | Ci on Cm API Rise Time | API PI Nm | Ci on Nm API Decay Time | Ci on Nm API FWHM Time | Ci on Nm API Peak Value | Ci on Nm API Rise Time | API PI Cm | Ci on Cym API Decay Time | Ci on Cym API FWHM Time | Ci on Cym API Peak Value | Ci on Cym API Rise Time |
|---|---|---|---|---|---|---|---|---|---|---|---|---|---|---|---|
| 1 | 344.7 | 687.4 | 1146.0 | 0.9 | 458.6 | 201.8 | 788.2 | 1248.2 | 1.4 | 460.0 | 334.6 | 741.4 | 1116.5 | 0.8 | 375.1 |
| 2 | 210.6 | 607.4 | 1210.0 | 0.2 | 602.7 | 154.6 | 635.8 | 1208.7 | 0.2 | 573.0 | 211.9 | 589.4 | 1215.9 | 0.1 | 626.5 |
| 3 | 132.6 | 682.5 | 1202.7 | 0.8 | 520.2 | 222.7 | 695.7 | 1221.5 | 1.2 | 525.9 | 124.5 | 679.2 | 1200.7 | 0.8 | 521.5 |
| 4 | 209.0 | 550.4 | 1110.0 | 0.9 | 559.5 | 341.2 | 483.0 | 1103.6 | 0.9 | 620.6 | 208.9 | 558.0 | 1108.2 | 1.1 | 550.3 |
| 5 | 242.4 | 850.0 | 1238.8 | 1.3 | 433.8 | 189.0 | 670.1 | 1338.6 | 1.8 | 668.5 | 236.9 | 874.0 | 1218.5 | 1.3 | 344.4 |
| 6 | 364.8 | 762.3 | 1090.5 | 0.7 | 328.2 | 194.9 | 710.2 | 1177.7 | 1.1 | 467.5 | 372.7 | 716.4 | 1047.1 | 0.7 | 330.7 |
| 7 | 183.3 | 700.6 | 1092.0 | 0.8 | 391.4 | 395.7 | 673.1 | 1238.3 | 1.5 | 565.2 | 179.9 | 695.6 | 1087.5 | 0.5 | 391.9 |
| 8 | 292.7 | 638.3 | 1258.7 | 1.4 | 620.3 | 220.7 | 670.4 | 1362.4 | 1.8 | 692.0 | 283.2 | 717.6 | 1202.5 | 0.8 | 484.9 |
| 9 | 215.0 | 699.6 | 1296.9 | 1.6 | 597.3 | 272.6 | 679.6 | 1326.8 | 1.8 | 647.3 | 213.3 | 673.8 | 1275.5 | 1.3 | 601.7 |
| 10 | 236.7 | 661.2 | 1279.3 | 1.1 | 618.1 | 215.0 | 772.0 | 1378.5 | 1.3 | 606.5 | 220.0 | 675.5 | 1237.5 | 1.1 | 562.0 |
| 11 | 554.2 | 660.2 | 1217.1 | 1.2 | 556.9 | 175.8 | 750.1 | 1334.7 | 1.8 | 584.6 | 525.8 | 638.7 | 1199.4 | 1.2 | 560.8 |

Kinetic image cytometry key:

Ci on Cm API Decay Time: Calcium on Cell Average Pixel Intensity Decay Time
Ci on Cm API FWHM Time: Calcium on Cell Average Pixel Intensity Full-Width Half Maximum Time
Ci on Cm API Peak Value: Calcium on Cell Average Pixel Intensity Peak Value
Ci on Cm API Rise Time: Calcium on Cell Average Pixel Intensity Rise Time
Ci on Nm API Decay Time: Calcium on Nuclear Mask Average Pixel Intensity Decay Time
Ci on Nm API FWHM Time: Calcium on Nuclear Mask Average Pixel Intensity Full-Width Half Maximum Time
Ci on Nm API Peak Value: Calcium on Nuclear Mask Average Pixel Intensity Peak Value
Ci on Nm API Rise Time: Calcium on Nuclear Mask Average Pixel Intensity Rise Time
Ci on Cym API Decay Time: Calcium on Cytoplasm Average Pixel Intensity Decay Time
Ci on Cym API FWHM Time: Calcium on Cytoplasm Average Pixel Intensity Full-Width Half Maximum Time
Ci on Cym API Peak Value: Calcium on Cytoplasm Average Pixel Intensity Peak Value
Ci on Cym API Rise Time: Calcium on Cytoplasm Average Pixel Intensity Rise Time Post-fixed image cytometry key:

API PI Wm: Average Pixel Intensity of Protein Image on Whole-Cell Mask
API PI Nm: Average Pixel Intensity of Protein Image on Nuclear Mask
API PI Cm: Average Pixel Intensity of Protein Image on Cytoplasm Mask

FIG. 15

ANALYSIS OF ACTION POTENTIALS, TRANSIENTS, AND ION FLUX IN EXCITABLE CELLS

PRIORITY

This application is a continuation of U.S. Ser. No. 15/947,490, filed Apr. 6, 2018, which is a continuation of U.S. Ser. No. 14/651,644, filed Jun. 11, 2015, which is a § 371 of PCT/US2013/075488, filed Dec. 16, 2013, which claims priority to U.S. 61/737,663, filed Dec. 14, 2012.

RELATED APPLICATIONS

This Application contains subject matter related to the subject matter of: U.S. patent application Ser. No. 12/454,217, filed May 13, 2009, published as US 2010/0289887 on Nov. 18, 2010; and, U.S. patent application Ser. No. 12/960,313, filed Dec. 3, 2010, published as US 2011/0318775 on Dec. 29, 2011.

BACKGROUND

The field includes the biological arts, such as cytometry, and particularly concerns processes, systems, and instruments for automatically measuring action potentials, calcium transients and ionic flux in excitable cells of humans and animals.

Excitable cells are those cells that are able to produce and respond to electrical signals and include neurons, muscle (skeletal, smooth, and cardiac muscle), and secretory cells. Like all cells, excitable cells maintain a resting membrane potential by controlling the levels of certain ions within the cell in relation to the external concentration of those same ions, establishing an electrochemical gradient across the membrane. However, certain stimuli can open specialized sodium channels (e.g., electrical stimuli, mechanical stimuli, or ligand binding) on the membrane of excitable cells that cause an increase in voltage from a negative hyperpolarized level across the membrane toward depolarization of the membrane. Once this membrane depolarization reaches a threshold level, voltage gated sodium channels open causing a rapid depolarization of the cell membrane followed by repolarization, which is referred to as an action potential. Action potentials can propagate along neurons for long distances and cause action potentials to occur in other excitable cells leading to various effects. For example action potentials in muscle cells lead to the rapid release of calcium from intracellular stores resulting in contraction of the cell.

Many fluorescent dyes which respond to changes in membrane voltage and ion concentrations (including but not limited to sodium, potassium, calcium, and chloride ions) are currently known. Using these dyes, researchers can make video recordings of a magnified field of view to observe changes in the intensity of the dyes when loaded into cells. Changes in the intensity of these dyes correlates to the activity of the action potentials (voltage sensitive dyes), calcium transients (intracellular calcium dyes), or ion flux across a membrane (e.g. sodium or potassium dyes). Cytometric analysis of video recordings of cells loaded with these dyes, which measures the change in the intensity of these dyes over time, can provide a quantitative assessment of the kinetics of the action potential, calcium transient or ion flux on a cell by cell basis. Chemical compounds, biological molecules (including but not limited to proteins, DNA and DNA constructs, RNAs, small non-translated RNAs such as siRNA, miRNA, or equivalent, or other molecules derived from biological material), electrical stimulation, or genetic manipulation can be applied to the cells prior to or during the recording. Using cytometric analysis methods the effect the compound, biological molecule, electrical stimulus or genetic manipulation has on the action potential, calcium transient, or ionic flux of the cell can be assessed quantitatively.

SUMMARY

It is desirable to be able to obtain images of multiple activities in excitable cells that occur simultaneously or in sequence in order to comprehensively and efficiently asses manifold activity of excitable sells. Voltage- and ion-sensitive fluorescent dyes are available with a variety of excitation and emission wavelengths, making it possible to load excitable cells with two or more dyes and collect video recordings from multiple dyes simultaneously. For example cultured cardiomyocytes can be simultaneously loaded with voltage and calcium sensitive dyes, each with distinct excitation and emission spectra. Video recordings of the fluorescent light emitted by each dye can be separated and provided to individual cameras. For example, one camera may capture the light emitted from the voltage sensitive dye and a second camera may capture the light emitted from the calcium sensitive dye. Preferably, the two cameras record from the same field of view and are triggered simultaneously. Analysis of the video recordings provides a quantitative assessment of the kinetics of the action potentials and the resulting calcium transients from each cell in the field of view.

An even larger number of dye labels for genes, RNAs and proteins may be used to obtain further information about the cells, but many require that the cells be first fixed. These labels include immunofluorescent and fluorescent in situ hybridization (FISH) labels, as well as their colormetric counterparts' immunohistochemical (IHC) and in-color in-situ hybridization (CISH) labels. For example, immunofluorescence for α-actinin may be utilized to observe and measure the degree of contractile apparatus organization and development in muscle cells (including cardiomyocytes) differentiated from stem cells. Immature muscle cells will have less organized α-actinin patterns than more mature muscle cells. Mutations in genes produce abnormal proteins, including ion channels in muscle cells (such as cardiomyocytes). Some of these mutations, such as mutations that cause long QT syndromes make patients prone to arrhythmias such as ventricular tachycardia and ventricular fibrillation, which can lead to sudden death. (Long QT syndrome refers to a lengthening of the interval between the QRS and T waves in the electrocardiogram.).

We have realized that the wavelength separation resulting from use of different labels to mark different activities of excitable cells affords the opportunity to visualize those activities by simultaneously acquiring images through separate optical channels.

Accordingly, processes, systems, and instruments are provided for producing, processing, and analyzing video recordings from two or more optical channels simultaneously, from a single sample, in an automated high-throughput manner. In some aspects, an automated high-throughput mode includes parallel processing of two or more wells automatically and sequentially in microtiter plates (e.g., with 96 or 384 wells).

An instrument produces simultaneous recordings from two or more distinct optical channels in an automated manner. Methods are executed for registering multiple optical channels and performing automated cytometric analysis of the registered recordings in order to extract measurements on a cell-by-cell basis.

In some aspects, an automated process fixes the sample after making the live cell recordings, labels the fixed sample for additional biomarkers, rescans the sample, detects and analyzes the fixed cell biomarkers, detects cells washed off during the fixation and labeling process, and registers and collates the live- and fixed-cell cytometry data together.

BRIEF DESCRIPTION OF THE DRAWINGS

FIG. 15 is a table of data of both kinetic and post-fixed image cytometry data collated to remove the cells missing from the latter.

DETAILED DESCRIPTION OF THE PREFERRED EMBODIMENTS

Figure 1:
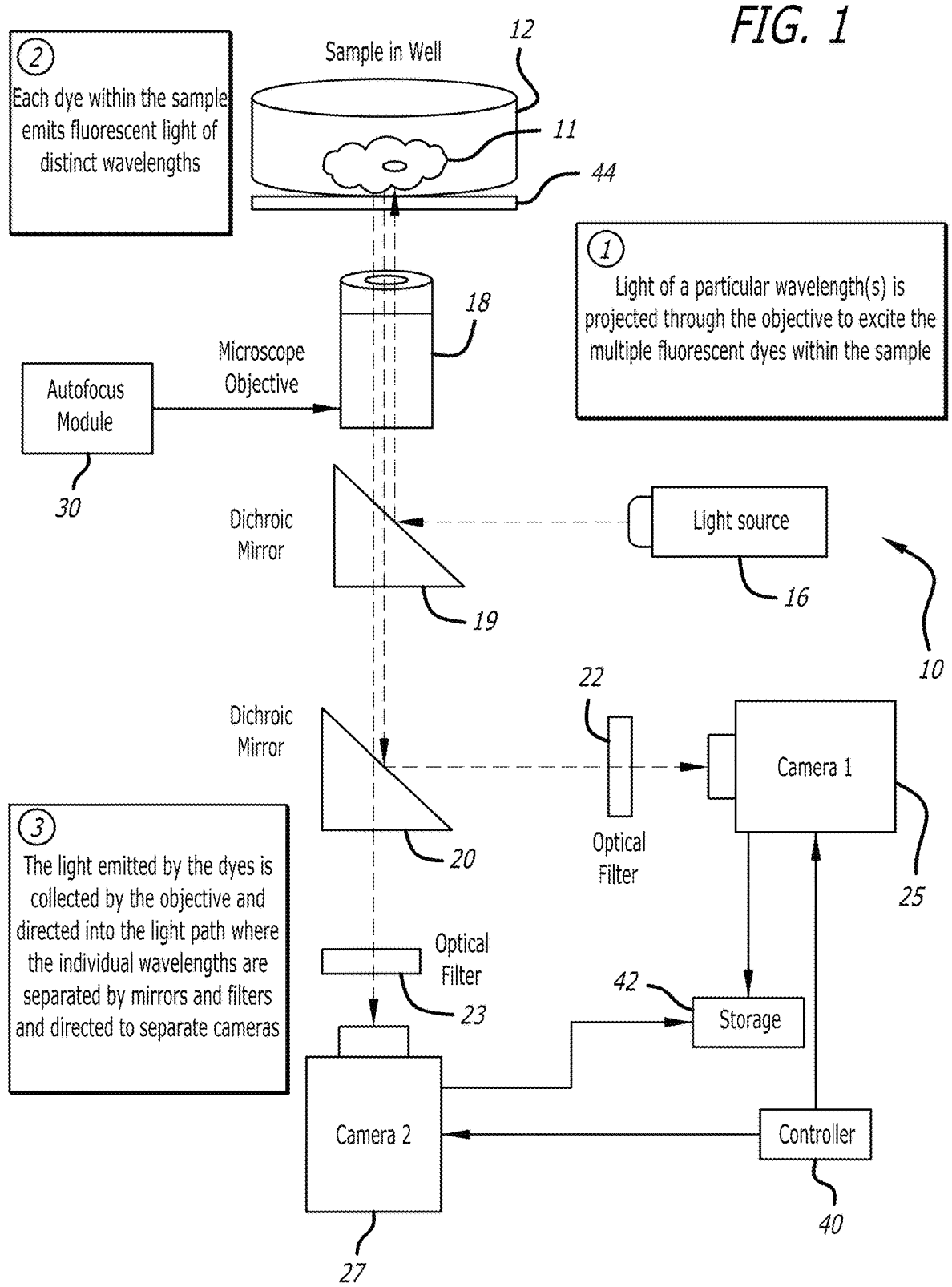
FIG. 1 is schematic illustration of an instrument and light path for obtaining simultaneous recordings from two or more distinct optical channels.
Figure 2:
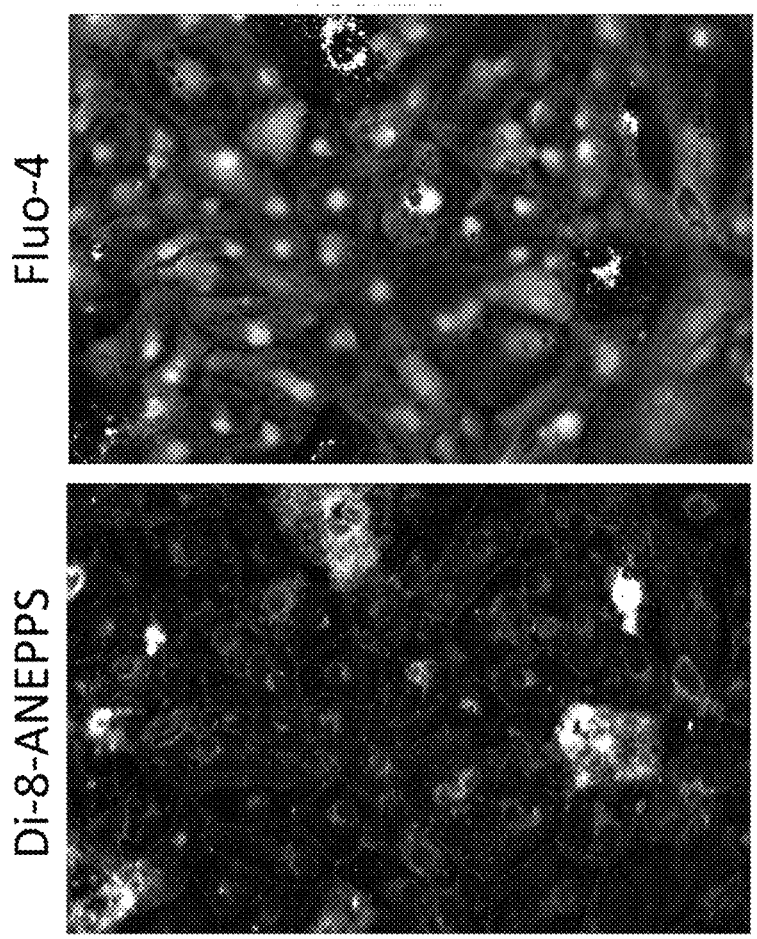
FIG. 2 includes images illustrating an example of cardiomyocytes loaded with calcium (Fluo-4) and voltage sensitive (di-8-ANEPPS) dyes. Recordings were made by two cameras simultaneously from the same field of view with each camera recording from a respective fluorescent wavelength

With reference to FIG. 1, an optical instrument 10, such as an automated microscope system, produces simultaneous recordings from two or more distinct optical channels. Preferably, the instrument 10 equipped to scan a sample 11 in or on a support 12 such as a multiwell (aka, microtiter) plate (any format, e.g., in a range from 6 to 1536 wells, though typically 96 or 384 well plates are used) containing live cells loaded with multiple fluorescent dyes in an automated manner. The instrument 10 includes an optical array coupled to multiple scientific cameras and includes a light source 16, a standard microscope objective 18, multiple mirrors, preferably dichroic mirrors, 19 and 20 defining the light path and optical filters 22 and 23 which may or may not be contained within automated filter wheels. Light of a specific wavelength or multiple wavelengths is directed from the light source 16 through the objective 18 onto the sample 11 to excite the fluorescent dyes within the sample cells. Fluorescent light with multiple wavelengths of light is then emitted from the sample 11; each emission wavelength correlates to a specific dye. This light is collected by the objective 18 and passes through a series of mirrors and filters which separate the distinct wavelengths of light and direct each one to a respective one of the cameras 25, 27. An autofocus module 30 constituted of hardware and software components moves the objective in the z position in order to focus the light onto a plane in the sample 11 which produces defined images in each of the cameras 25 and 27. The cameras are electrically triggered by a controller 40 to start and stop recording at the same time in order to produce simultaneous recordings. The cameras record to an electronic storage device 42 where the data is stored prior to processing and analysis. Two images produced simultaneously by the instrument are seen in FIG. 2.

In some aspects, the instrument of FIG. 1 is fitted with a motorized stage 44 that holds the multiwell plate 12 and positions the sample 11 to be imaged over the objective 18. Once imaging is completed for a given area the stage 44 moves the plate 12 to the next sample area to be imaged. The next area can be a different area of the same well or an area within a new well on the plate. A user-defined map is preprogrammed and describes the areas within each sample plate that are to be imaged. Once started, the instrument automatically images each defined area, moving from one area to the next after recording for a defined period of time.

Figure 3:
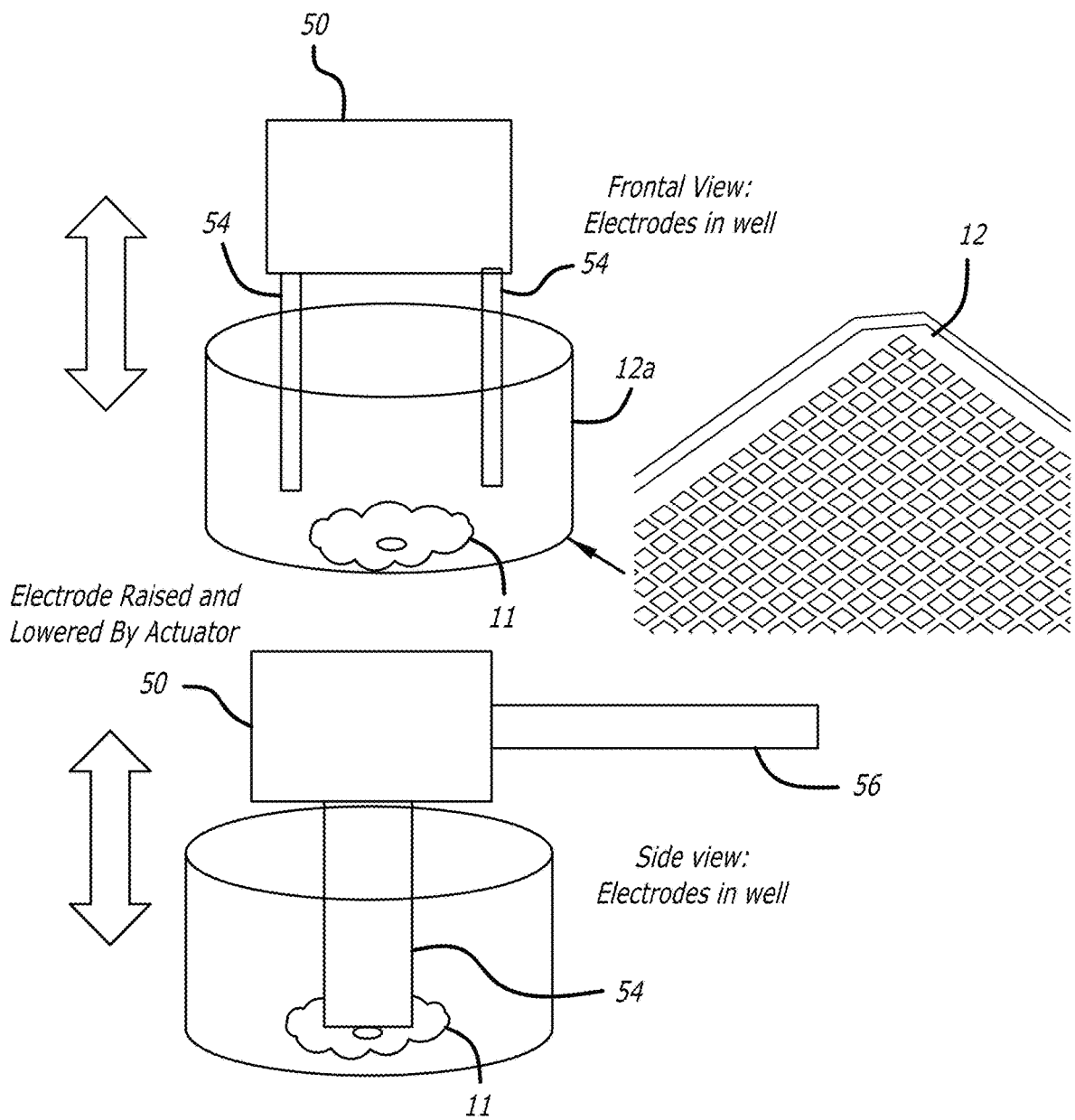
FIG. 3 is schematic illustration of an electrical stimulator arm for introducing electrodes into a well of a multiwall plate.

With reference to FIG. 3, a motorized stimulator arm 50 attached to the stage 44 automatically lowers electrodes 54 into the sample well 12a of the multiwall plate 12 being imaged in order to electrically stimulate the cells. When the arm 50 is lowered into the well 12a, electrical pulses with a defined voltage, duration, shape, and frequency can be applied to the cells. Following completion of the recording in one area, the electrodes 54 are raised to allow the stage to move to the next area to be imaged. Once the stage has moved to the next area to be imaged the electrodes 54 are lowered again. The application of electrical stimuli is coordinated with the triggering of the cameras so that the exact point in the recording when stimulation is applied can be determined.

In some aspects, the motorized stage which holds the sample is enclosed within an incubation chamber in order to preserve cell physiology and maintain viability. Temperature, carbon dioxide, and oxygen levels are maintained at user defined levels within the incubation chamber. Temperature is controlled by heater elements which are activated and deactivated by a thermostat. Carbon dioxide and oxygen levels are maintained via an electronic feedback loop which consists of carbon dioxide and oxygen sensors which control electronic valves that introduce either carbon dioxide or oxygen from gas cylinders into the incubation chamber as needed to maintain preset levels.

Figure 4:
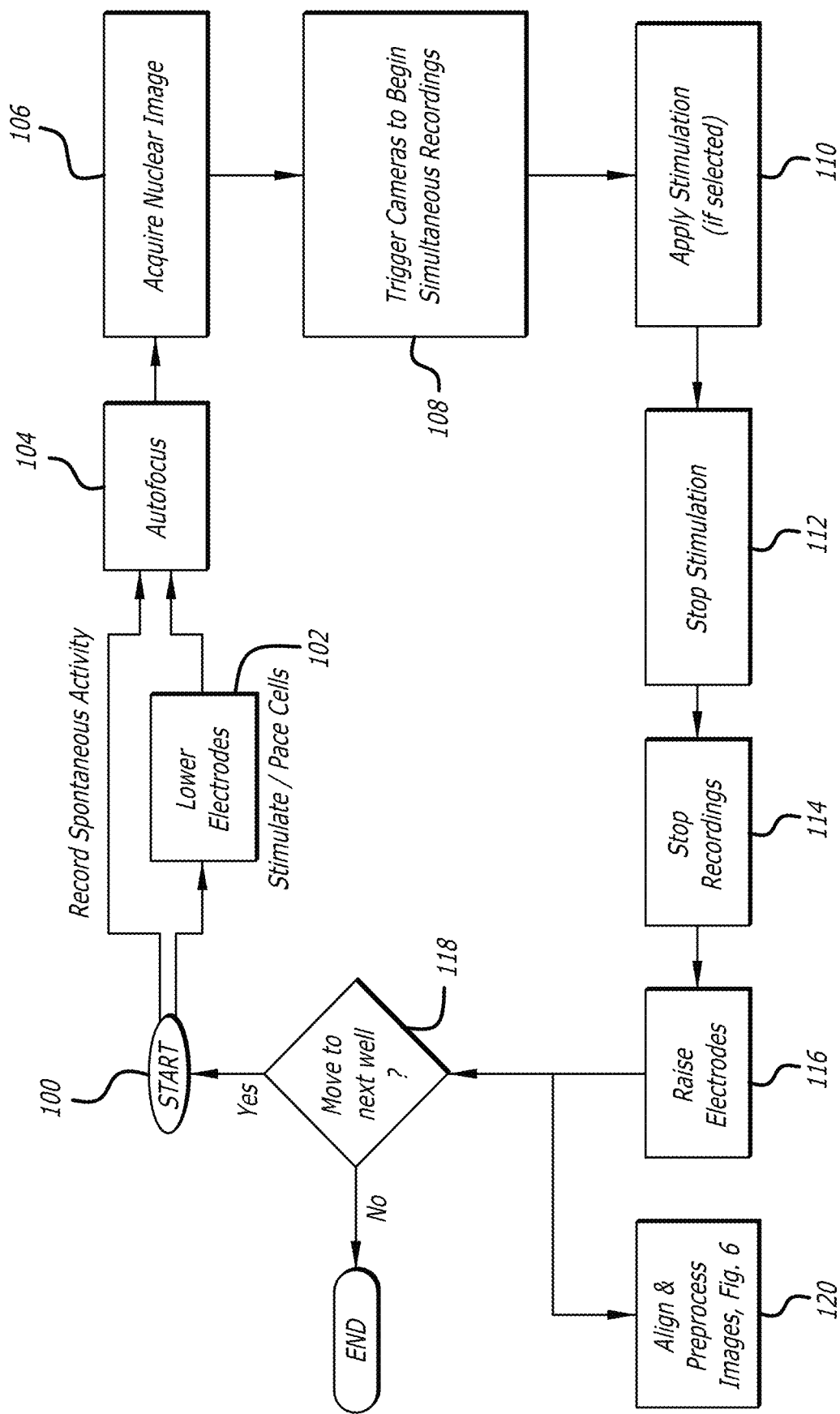
FIG. 4 is flow diagram illustrating a process for collecting simultaneous recordings from two or more distinct optical channels using the instrument of FIG. 1.

An example of a process for collecting video recordings in a high throughput manner using this instrument is illustrated in FIG. 4. The process, which includes collecting simultaneous recordings from the example of cardiomyocytes loaded with voltage and calcium sensitive fluorescent dyes is used for illustration only. Any excitable cell and any combination of voltage or ion sensitive dyes could be substituted; dye free imaging of the cells such as observing movement under bright field could also be incorporated. With reference to FIG. 4, a multi-well plate containing cardiomyocytes which have been loaded with a nuclear dye (i.e. Hoechst) and two or more fluorescent dyes which respond to membrane voltage fluctuations and calcium transients and which have different and distinct excitation and emission spectra are loaded onto the stage of the instrument illustrated in FIG. 1. The instrument is controlled by a control mechanization executed by the controller 40, which may include, for example, a computer. In some aspects, the video recordings are stored on the hard drive(s) of the same computer. The control mechanization enables a user to define parameters for the scan, which include, without limitation, the number of fluorescent channels to be imaged, the excitation wavelength(s), light intensity, camera frame rates, duration of the recording stimulation protocol to be applied (voltage, duration, shape, and frequency of the electrical pulses applied to the cells), and the plate map defining which wells on the plate recordings will be made from. Once started at 100 the motorized stage moves the first well to be imaged over the objective. If electrical stimulation is to be applied the electrodes are lowered into the well at 102. The instrument then autofocuses at 104 using a nuclear signal and collects an image of the cell nuclei at 106. The instrument then begins the simultaneous video recordings by triggering two separate cameras at 108. If the user has selected to apply electrical stimulation to the cells that protocol is activated at 110 shortly after the recordings begin. Following completion of the stimulation protocol at 112, the cameras stop recording at 114, and the electrodes are raised at 116. At 118, if there are more wells to image the stage moves the well plate so that the next well to be imaged is positioned over the objective and the process is repeated.

Figure 5:
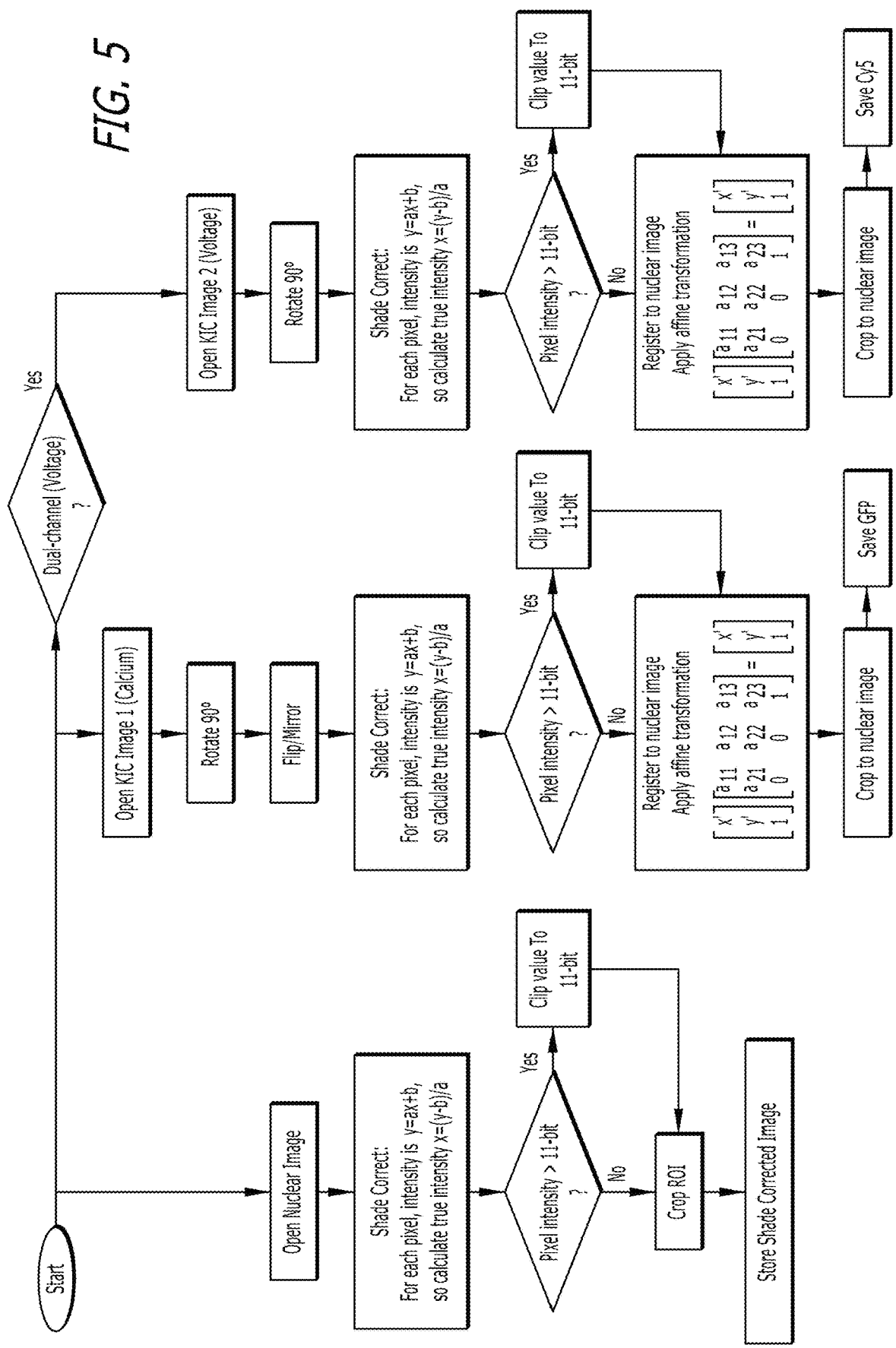
FIG. 5 is a flow diagram illustrating a process by which nuclear, calcium and voltage images are shade corrected, magnification corrected and registered.

In some aspects, at 120 the recordings are preprocessed prior to analysis to register the recordings from each camera. A control routine such as that illustrated in FIG. 5 is used to correct for mirroring, X-Y shift, rotation, and magnification differences in the recordings captured by different cameras recording from the same field of view which are introduced by the light path, camera position, and chromatic aberration. Registration is performed using a predetermined set of parameters that are collected by imaging a multiwell plate containing multispectral beads either before or after the video recordings are produced. An analysis routine analyzes the images of the multispectral beads, determines the manipulations that need to be made in order to the register the recordings. Once the recordings are registered they are cropped so that only the areas of the image that appear in all channels are maintained.

The routine illustrated in FIG. 5 performs: image orientation correction (e.g., correction for mirror imaging of the two cameras), correction of shade distortion (AKA flat field correction), image registration (correction for lateral misalignment, differences in magnification, and correction for rotation between the cameras), and final cropping to make the images the same pixel size after magnification correction. Prior to execution of the routine, the following calibration steps are performed:

1. The orientation of each image with respect to the others is observed and recorded. For example, a dichroic mirror is used to send longer wavelength fluorescence emission for voltage to one camera and shorter wavelength emission for calcium to another camera, resulting in a mirror orientation of one image to the other. The cameras can further be mutually rotated. The orientation of the nuclear image relative to the other two depends on which camera images it.

2. A shade correction calibration is performed by measuring the shade distortion (deviation from uniform intensity with a uniform intensity specimen, typically a flat piece of glass, or mirror) across the image, and collecting a series of images at known different intensities to correction for deviation from linearity and ensure that the intensity response curve (plot of output intensity as a function of input intensity) crosses the Y-intercept at zero.

3. An image of multicolor fluorescent beads, fluorescing at a minimum at the same colors as the fluorescent dyes to be used in the experiment, is collected at each of the emission wavelengths of the dyes to be used in the experiment. An automated registration software algorithm finds the X- and Y-lateral shifts, the differences in magnification, and the rotation of each of the other images relative to the bead image of the nuclear color.

The routine illustrated in FIG. 5 then corrects image orientations, performs shade and linearity correction, registers the images to the nuclear image, and crops the images to the same size. Magnification correction is needed because chromatic aberration causes images of different colors to be magnified differently.

After calibration, the routine of FIG. 5 is executed as follows.

1. Image orientation correction. For single-channel KIC (kinetic image cytometry), the calcium and voltage images are aligned to the nuclear image (for two cameras, the image on one camera is the mirror of the image on the other camera due to splitting the light with a dichroic mirror). Using the information stored during calibration, the calcium and voltage images are flipped/rotated to align with the nuclear image.

2. Shade correction. All microscopes exhibit some distortion of the illumination intensity across the field of view. This is called shade distortion. For example, consider a fluorescent bead in focus at the center of the camera field of view. If the stage is moved so that the sample is at the edge of the field of view, the bead's intensity is usually different (usually lower intensity) due to shade distortion. To compensate for this, the response of each pixel on the camera is modeled as $$y = ax + b$$

where 'y' is raw image intensity, 'x' is the corrected intensity, 'b' is the value needed to obtain a Y-intercept of zero after correction, and 'a' is the slope needed to correct each pixel to the same intensity. The values of 'a' and 'b' are calculated for every pixel on the camera's CMOS by linear regression when varying Lumencor intensity for a fixed exposure time. The corrected intensity is then calculated by inverting the relationship $$x = (y - b)/a$$

The values of 'a' and 'b' also vary with excitation wavelength, and the calibration is also done for every wavelength on the Lumencor. From the linear regression, 'hot' and 'dead' pixels would have calculated values of a=0. Any values of a=0 are changed to a=1, so that 'dead' pixels remain close to 0, and 'hot' pixels remain close to saturation. Any corrected pixels greater than the maximum intensity allowed by the bit dept of the image are set to the maximum intensity; e.g., in an 11-bit image, pixel intensities greater than 2,047 are set to 2,047.

3. Image registration. In the dual-channel KIC, images in the two distinct cameras may be linearly shifted and rotated relative to each other (X- and Y-shift). Moreover, there are magnification differences between the different colors of nuclear, calcium and voltage fluorescent dyes due to chromatic aberration. Finally the cameras may not be perfectly aligned with respect to rotation. Thus for registration, an affine transformation is calibrated beforehand using multi-color beads and the other images are registered to the nuclear image serves. The affine transformations compensate for linear translation, rotation, and magnification (scaling) all at once for all other colors relative to the nuclear image. For every pixel coordinate (x,y) in the original image, a new set of coordinates (x',y') are calculated according to:

$$\begin{bmatrix} x' \\ y' \\ 1 \end{bmatrix} \begin{bmatrix} a_{11} & a_{12} & a_{13} \\ a_{21} & a_{22} & a_{23} \\ 0 & 0 & 1 \end{bmatrix} = \begin{bmatrix} x \\ y \\ 1 \end{bmatrix}$$

4. ROI cropping. After registration, magnification correction creates images of different sizes in pixels and these images are cropped so that the resulting images stored to the hard drive are all the same size.

Figure 6:
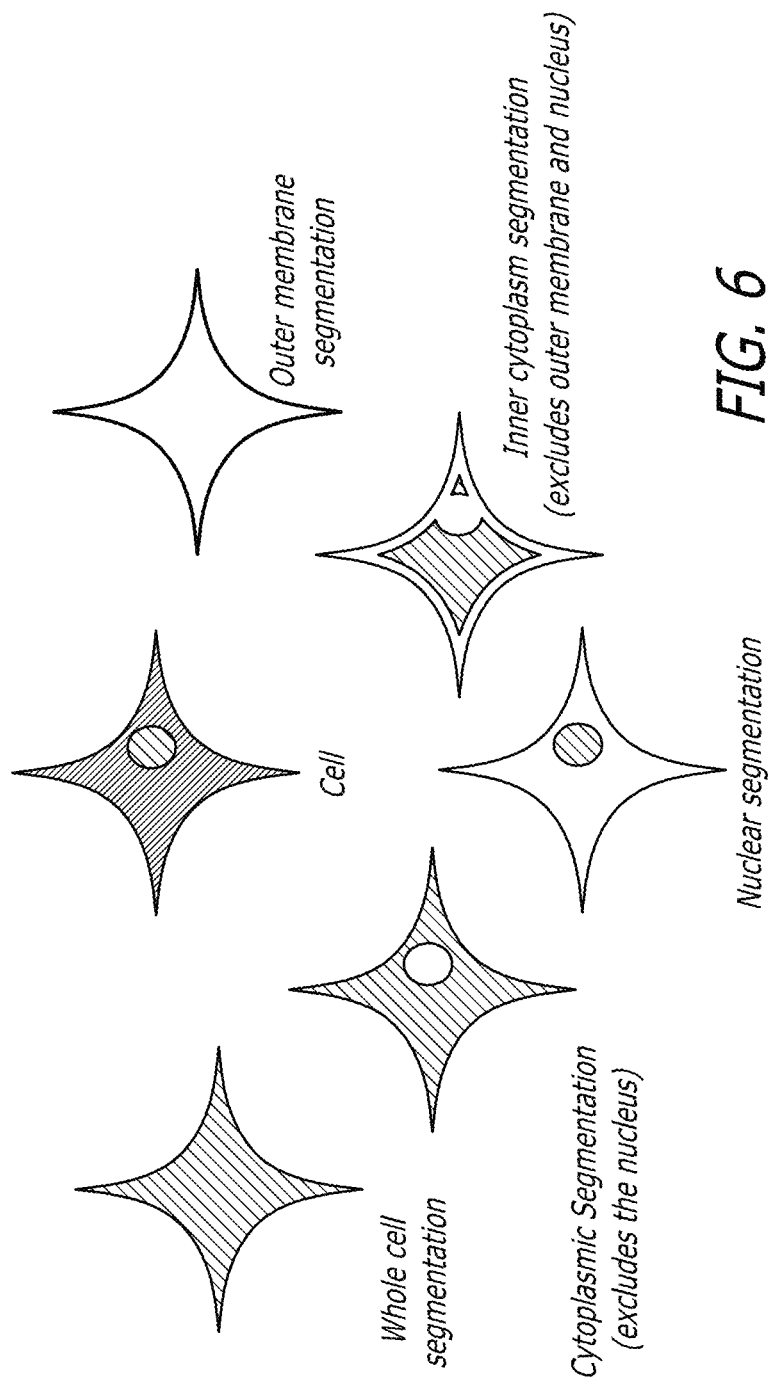
FIG. 6 is a diagram demonstrating periphery masks and examples of subcellular mask applied to cells being imaged.

The processed recordings are then analyzed using automated cytometry routines represented by FIG. 6 which identify, segment and index each cell in the field of view to produce cell periphery masks and masks defining subcellular regions using known methods which combine data from two or more optical channels in order to define the boundaries of the whole as well as distinct regions within the cell. The masks are applied to each image in each recording and the intensity of the dyes in each cell is calculated for each frame of the recording.

Figure 7A:
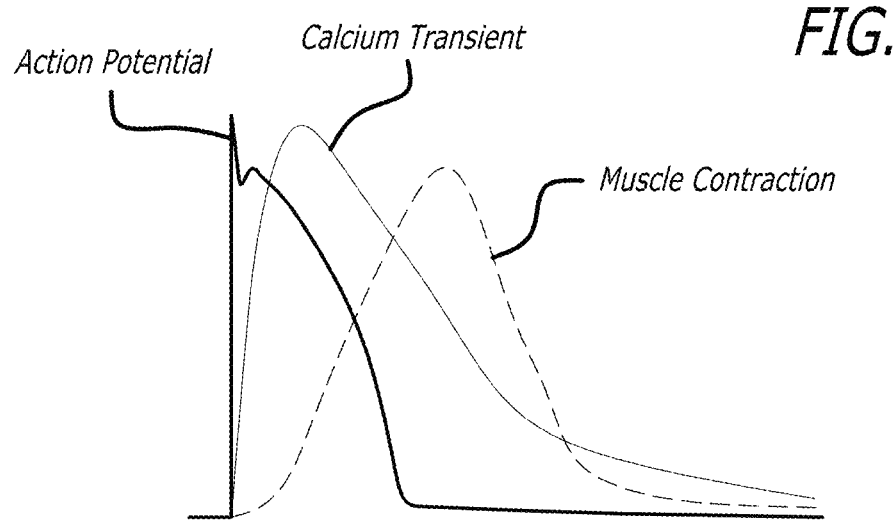
FIG. 7A is a waveform diagram illustrating an excitation-contraction coupling model which describes a relationship between action potential and calcium transient in cardiomyocyte contraction.
Figure 7B:
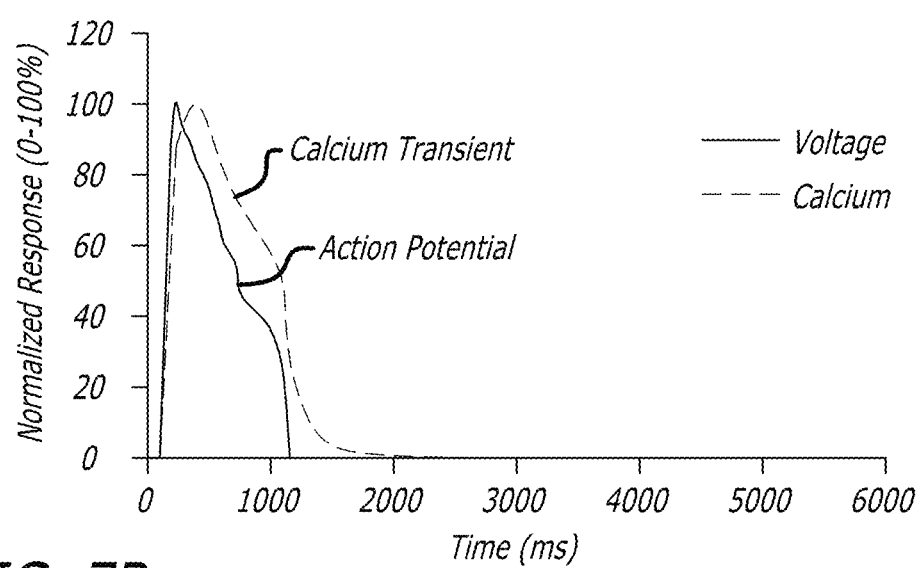
FIG. 7B is a diagram illustrating curves which describe the action potentials and calcium transients of cardiomyocytes collected.

As per FIGS. 7A and 7B, the change in intensity is then plotted against time (based on frame number and frame rate at acquisition) and the resulting plot represents the kinetics of the action potential, calcium transient, or ionic flux depending on which dye is being analyzed. Corrections can be made prior to analysis of the kinetics to account for artifacts such as photobleaching of the dyes. The fluorescent dye that is sensitive to voltage across the membrane of each cell is more sensitive to photobleaching than most other fluorescent dyes. Thus, a straight line is fit to the data and the straight-line parameters are used to correct for the gradual decrease in intensity caused by photobleaching. The fluorescent dye that is sensitive to voltage across the membrane of each cell decreases in intensity with the increase in voltage that occurs during the action potential. Thus, the intensity vs. time data is inverted (each intensity is subtracted from the maximum intensity).

Figure 8:
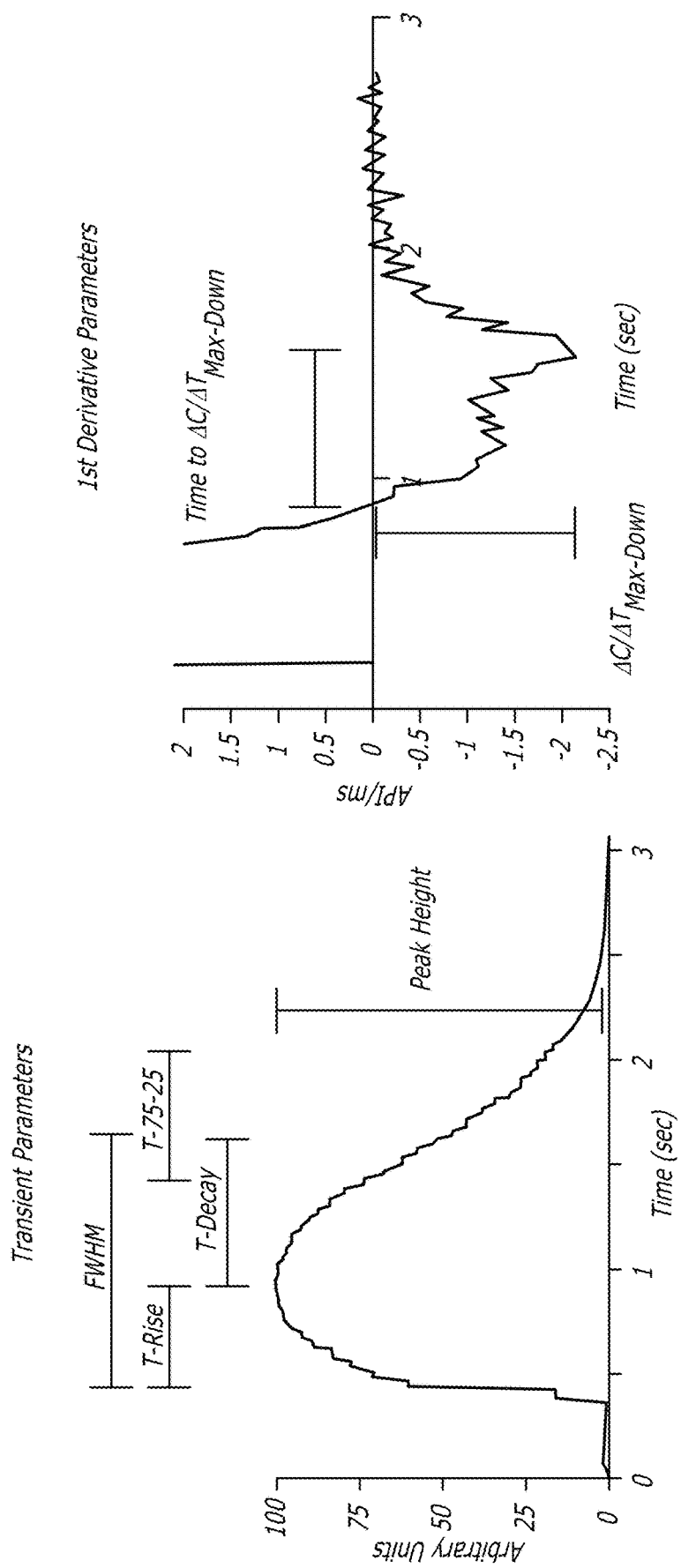
FIG. 8 includes diagrams illustrating measurements extracted from curves describing the action potential, calcium transient, or ion flux.

With reference to FIG. 8, measurements that describe the shape and duration of the action potential, calcium transient, and/or ionic flux are then automatically extracted from the plots of intensity versus time. These measurements include, but are not limited to:

Direct measurements such as:

Peak height—the maximum point in the curve describing the action potential, calcium transient, or ion flux;

Rise Time—AKA TRise or T-Rise, the time elapsed from the 50% point on the up stroke of the transient to the 100% point or the maximum of the action potential, calcium transient, or ion flux;

Decay Time—AKA TDecay or T-Decay, the time elapsed from the transient maximum to the 50% point on the downstroke of the action potential, calcium transient, or ion flux;

Full Width Half Maximum—AKA FWHM—the time elapsed from the 50% point of the upstroke to the 50% point of the downstroke of the action potential, calcium transient, or ion flux; and T75-25—AKA T-75-25, the time elapsed from the 75% point of the downstroke to the 25% point of the downstroke of the action potential, calcium transient, or ion flux.

Parameters measured from 1st derivatives such as:

$\Delta C/\Delta tmax$-down—defines the maximum negative slope achieved during the downstroke of the of the action potential, calcium transient, or ion flux;

Time to $\Delta C/\Delta tmax$-down—the time elapsed from the transient maximum to the maximum negative slope of the transient downstroke of the action potential, calcium transient, or ion flux;

$\Delta C/\Delta tmax$-up—defines the maximum positive slope achieved during the upstroke of the transient of the action potential, calcium transient, or ion flux; and Time to $\Delta C/\Delta tmax$-up—the time elapsed from the beginning go the transient to the maximum positive slope of the transient upstroke of the action potential, calcium transient, or ion flux.

Figure 9:
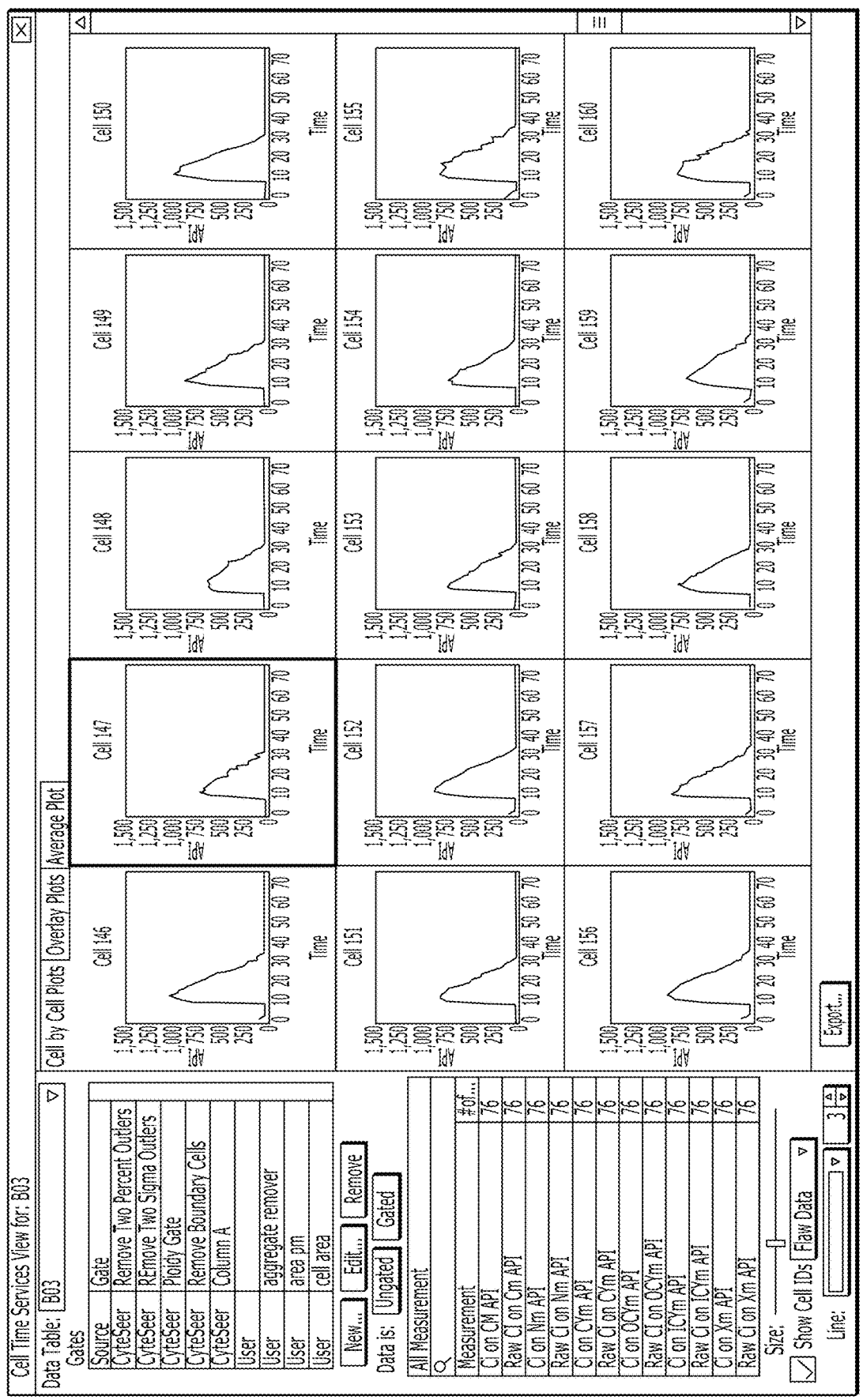
FIG. 9 is screen shot containing plots of multiple calcium transients in multiple cells from the same field of view.
Figure 10:
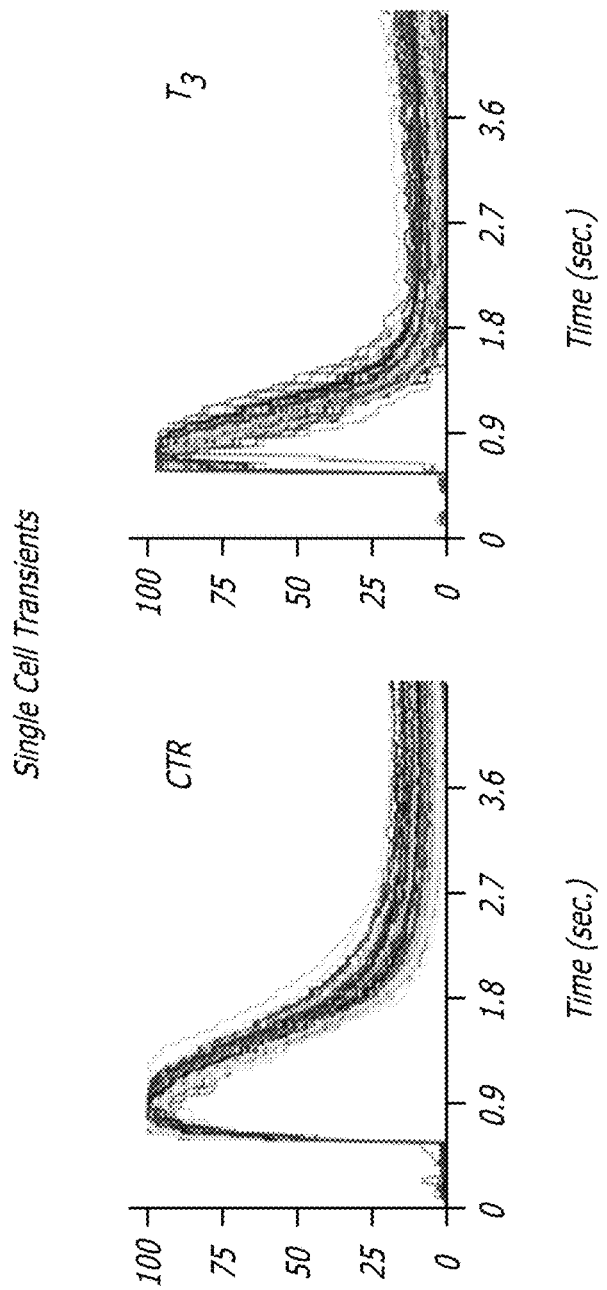
FIG. 10 shows plots of calcium transients of about 100 cells from the same image overlaid on top of each other.

As per FIG. 9, the transients from the same condition or well can be plotted individually. Alternatively, many transients can be plotted on top of each other as per FIG. 10.

Figure 11:
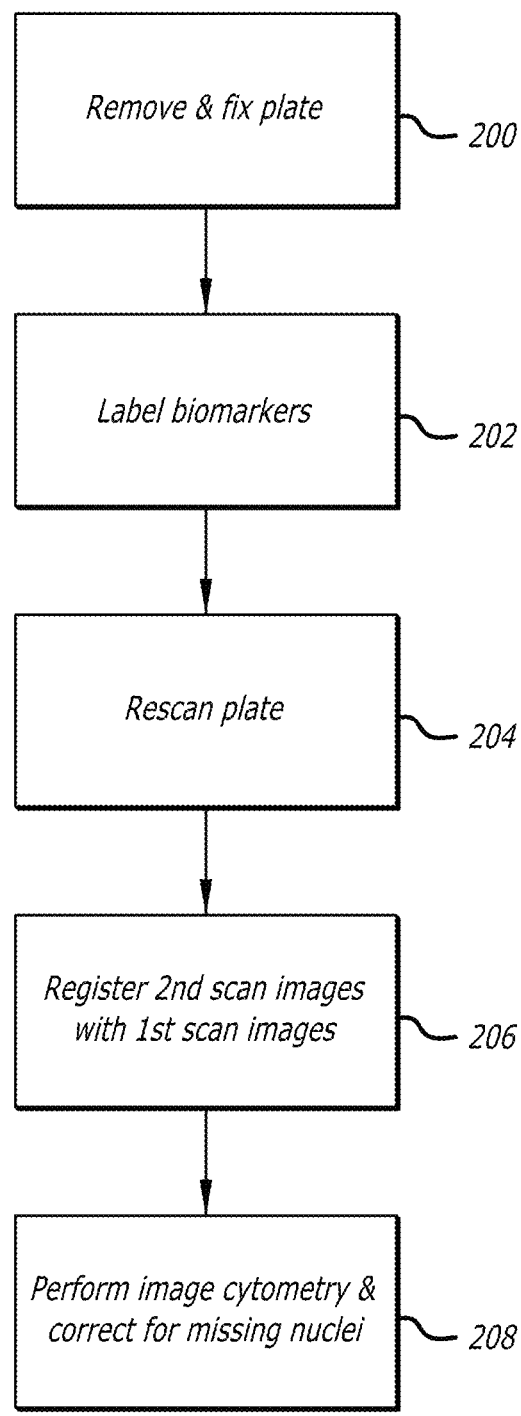
FIG. 11 is a flow diagram illustrating post-kinetic fixation and labeling of biomarkers, rescanning the same plate/cells, performing fixed image cytometry and collating the fixed image cytometry cell-by-cell with the transient image cytometry.

With reference to FIG. 11, there are many proteins, RNA sequences and DNA sequences that can only be labeled by first fixing (killing) the cells and thus cannot be carried out during live kinetic image cytometry. To solve this problem, we use the process of fixing the cells at 200, labeling them at 202, rescanning them at 204, registering the images at 206, and then performing image cytometry analysis at 208 by detecting the cells/nuclei lost during fixation and collating the kinetic image cytometry data set together with the fixed image cytometry data set for each cell.

Figure 12:
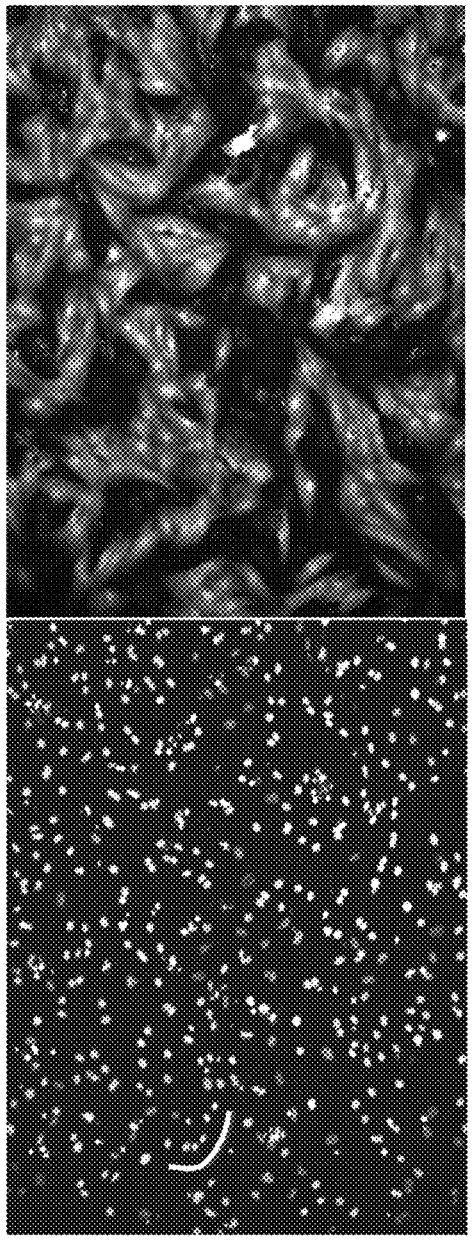
FIG. 12 compares a calcium kinetic image cytometry average image with a post-fixation image labeled for cardiomyocyte biomarker α-actinin.
Figure 12:
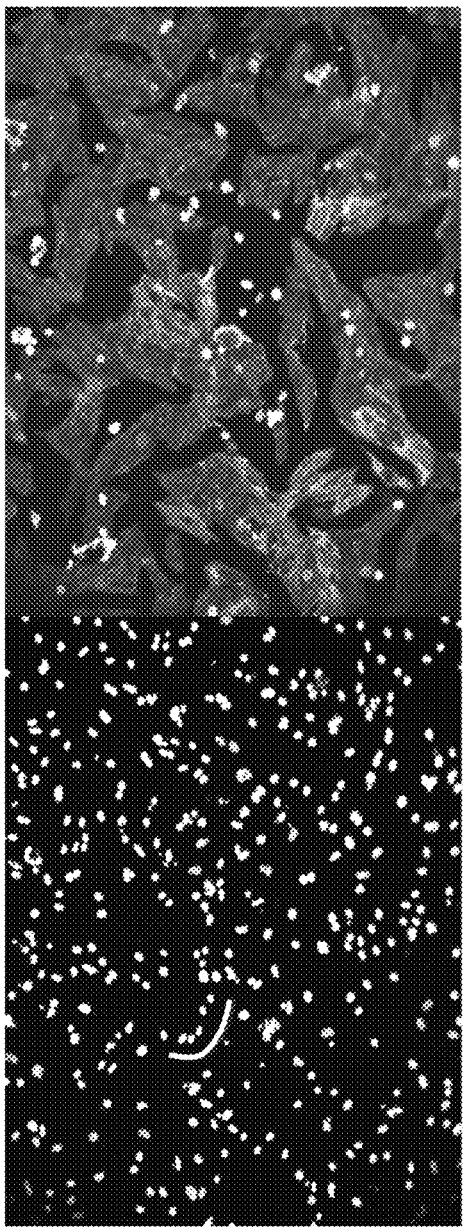
Figure 13:
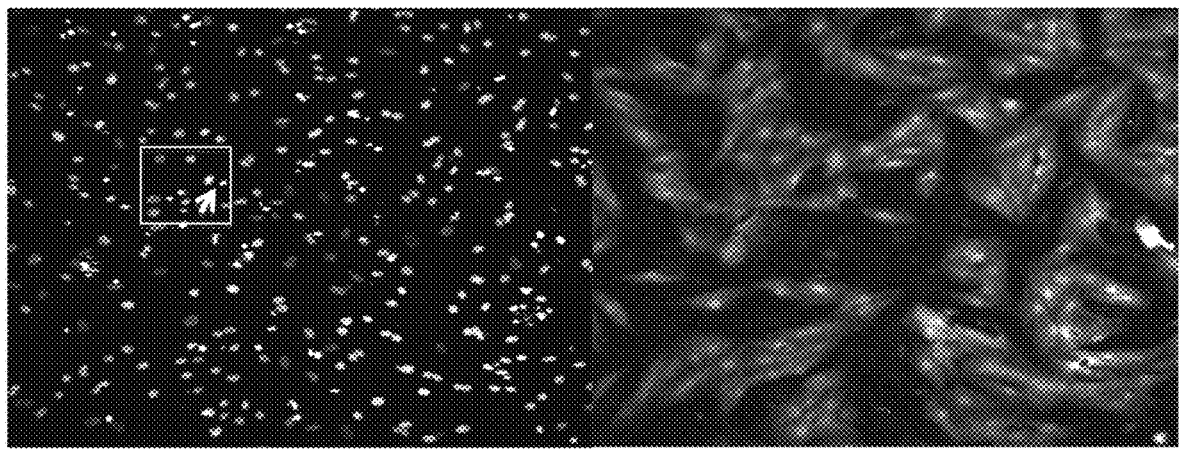
FIG. 13 illustrates segmentation of averaged kinetic calcium and post-fixed biomarker images and also demonstrates some cells lost during fixation.
Figure 13:
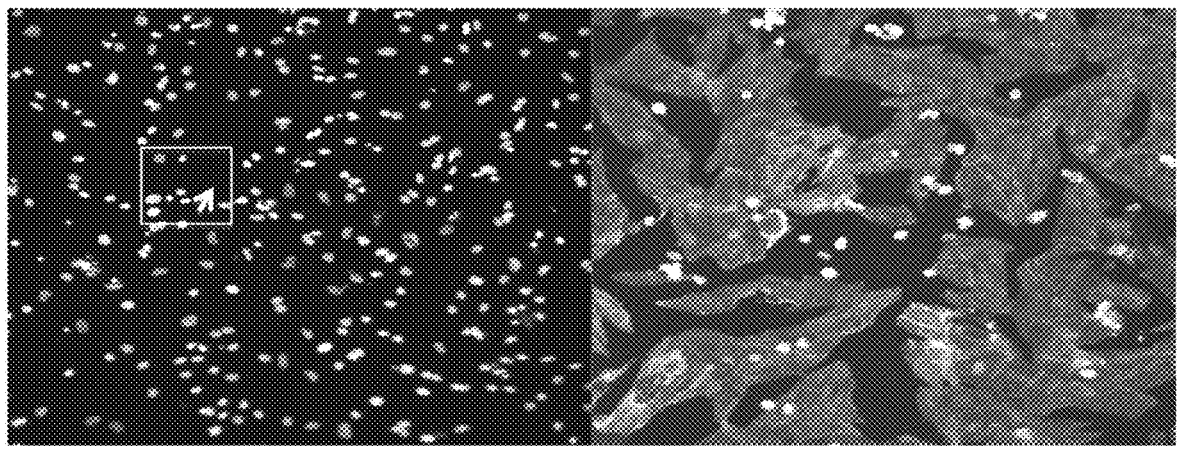
Figure 13:
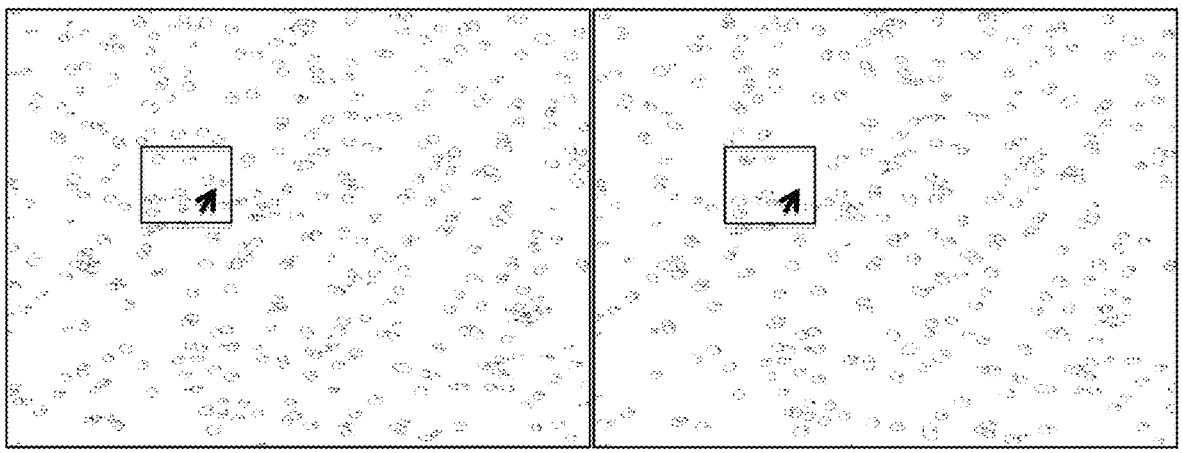
Figure 14:
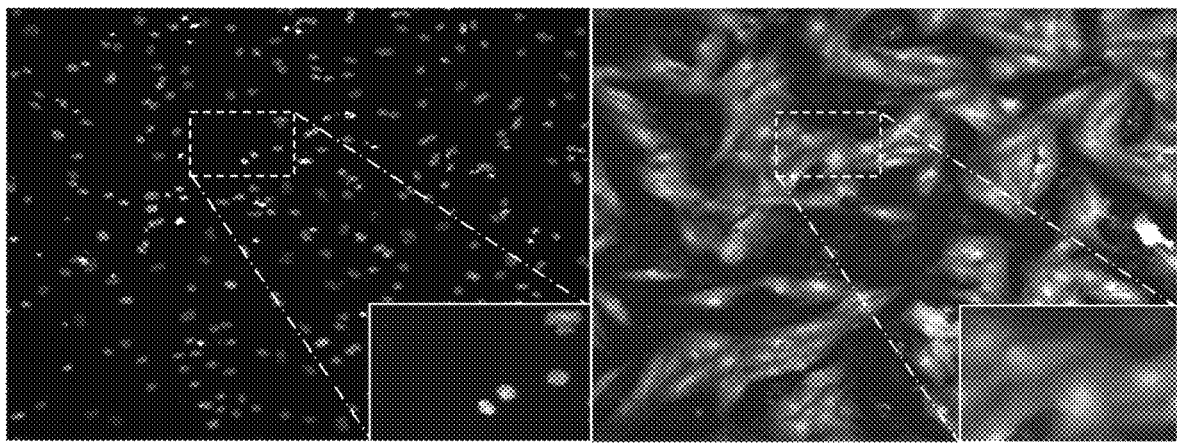
FIG. 14 illustrates removal of the cells missing from the post-fixation data set from the kinetic image cytometry data set.
Figure 14:
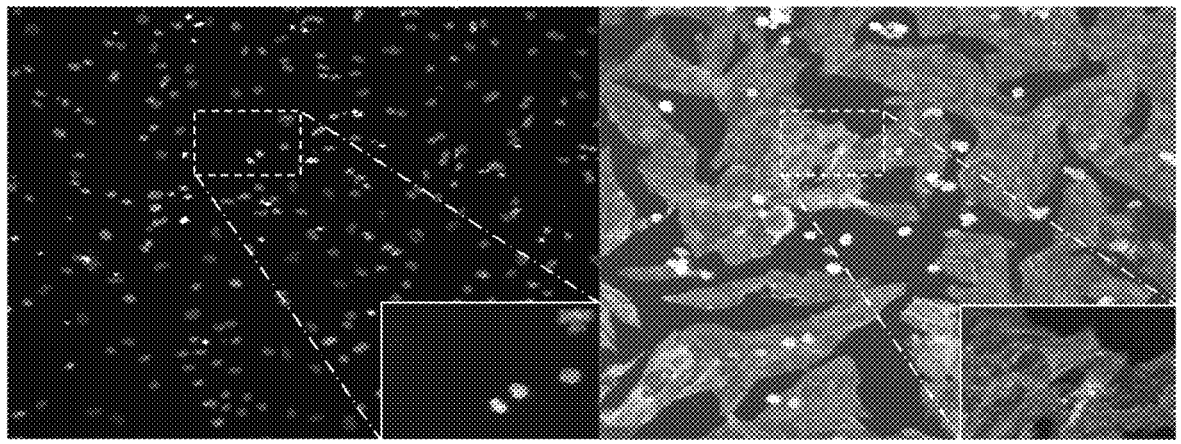
Figure 14:
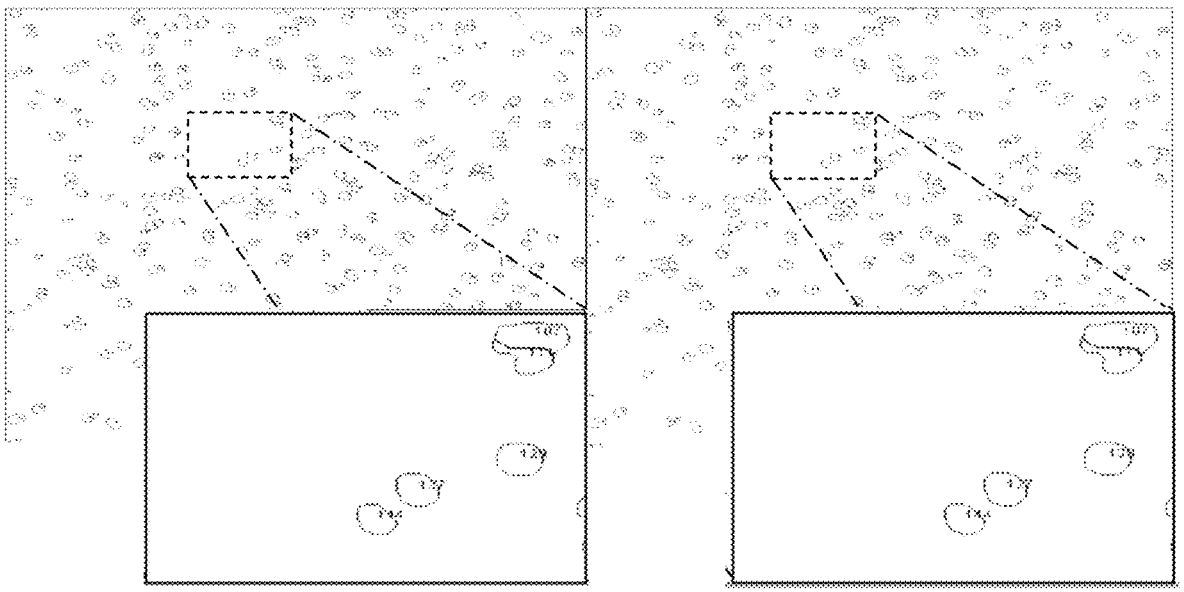

An example of an averaged kinetic image cytometry calcium video and a post-fixation image of the same cardiomyocytes labeled for cardiomyocyte biomarker α-actinin are shown in FIG. 12. FIG. 12 shows calcium and nuclear images of neonatal rat ventricular myocytes from the live cell scan and the same region after fixation and immunostaining for the cardiomycoyte marker α-actinin and the nuclei. The two pairs of images are shifted relative to each other due to misalignment during repositioning of the plate on the same microscope stage after fixing and staining. The curved line (arc) shows a common area between the two pairs of images. The same image pairs are shown segmented and registered in FIG. 13, and the rectangle and arrows show the same regions and nuclei washed off during fixation and labeling in the fixed image, respectively. FIG. 14 demonstrates comparison of the kinetic image cytometry and the fixed image cytometry data sets to locate the missing cells and delete them from the kinetic image cytometry data set in as a step in forming a merged kinetic-and-fixed image cytometry data set for convenient automated analysis. The nuclei demonstrate the underlying merged data by displaying the same number labels. FIG. 15 illustrates an example data table of both kinetic and post-fixed image cytometry data collated after removal of the cells missing from the latter are shown, along with a key for the measurements for the two data sets.

We claim:

1. A method executable by an instrument for producing simultaneous video recordings of a magnified field of view from multiple optical channels in order to create recordings of a sample containing cells loaded with two or more fluorescent dyes designed to respond to action potentials, calcium transients, ion concentrations, or a flow of ions across a cell membrane, wherein the instrument comprises:
   an optical path including a light source, microscope objective, mirrors, optical filters;
   a motorized stage that positions a region of the sample to be imaged above the objective;
   an autofocus module that moves the microscope objective in relation to the sample in order to focus an image by collecting a stack of images, each image in the stack being collected at a different focus position, calculating a degree of focus or a sharpness index, deriving a best focus position based on the degree of focus, and setting focus to a best focus position, wherein the images in the stack are either of a different fluorescent color and wherein an automatic filter changer changes a filter after autofocus to collect a corresponding live cell channel, or wherein the images in the stack are collected on the same fluorescent channel as a corresponding live cell channel;
   an incubation chamber that contains the sample and that maintains temperature, carbon dioxide, and oxygen at preset levels;
   a control system for recording two or more videos simultaneously to record two or more varying levels of light, each of which corresponds to two or more different intracellular components;
   whereby the recordings made by the instrument are processed and analyzed to provide quantitative measurements including one or more of cellular action potentials, calcium transients, ion concentrations, and/or flow ions across a membrane, by method steps comprising:
   maintaining temperature and carbon dioxide at present levels in the incubation chamber;
   moving the microscope objective in order to autofocus the light onto a plane in the sample which produces defined digital images;
   correcting for mirroring, X-Y shift, rotation, and magnification differences between the video recordings of different channels recorded from the same field of view;
   segmenting the videos of the cells into cell masks to define the area and boundaries of individual cells;
   generating measurements from the cell peripheries and cell masks of changes in intensity over time of the fluorescent dyes;
   plotting the changes in intensity of the fluorescent dyes versus time; and,
   extracting from plotted changes in intensities measurements that characterize shape and duration of the cellular action potentials, calcium transient, ion concentrations, and/or ion flow.

2. The method of claim 1, further including a stimulator arm to automatically move a pair of electrodes into wells of a multiwell plate for applying a user-defined electrical stimulation protocol to the cells.

3. The method of claim 2, further including maintaining oxygen at present user-defined levels in the incubation chamber.

4. The method of claim 3, further including segmenting the videos of the cells and labeling subcellular regions of the cells from two or more optical channels in order to define the distinct subcellular regions within each cell, and
   generating measurements from the cell periphery and subcellular masks of changes in intensity over time of the fluorescent dyes.

5. The method of claim 4, further including fixing the cells and labeling fixed cells for additional cellular molecules.

6. The method of claim 5, further including scanning the sample a second time and recording images of colors of labels in the fixed cells.

7. The method of claim 6, further including registering the images from the fixed scanning to the images and video recordings of the live scanning.

8. The method of claim 7, further including segmenting the images of the fixed scanning to detect the fixed cells and subcellular regions, detecting missing cells washed off during the process of fixing and labeling, and recording measurements of the fixed cell labels in the cellular and subcellular regions.

9. The method of claim 8, further collating the live cell and fixed cell cytometric measurements into a single data set to study and compare the fixed cell and live cell labels together.

* * * * *